US010191180B2

(12) United States Patent
Yaish et al.

(10) Patent No.: US 10,191,180 B2
(45) Date of Patent: Jan. 29, 2019

(54) LARGE SCALE GAS ELECTRON MULTIPLIER AND DETECTION METHOD

(71) Applicant: Lingacom Ltd., Tel Aviv (IL)

(72) Inventors: David Yaish, Tel Aviv (IL); Yosef Kolkovich, Tel Aviv (IL); Amnon Harel, Haifa (IL)

(73) Assignee: Lingacom Ltd., Tel Aviv (IL)

( * ) Notice: Subject to any disclaimer, the term of this patent is extended or adjusted under 35 U.S.C. 154(b) by 614 days.

(21) Appl. No.: 14/966,084

(22) Filed: Dec. 11, 2015

(65) Prior Publication Data

US 2016/0170078 A1    Jun. 16, 2016

Related U.S. Application Data

(60) Provisional application No. 62/091,021, filed on Dec. 12, 2014, provisional application No. 62/091,090, filed on Dec. 12, 2014.

(51) Int. Cl.
*G01T 1/26* (2006.01)
*G01V 5/00* (2006.01)
*G01V 13/00* (2006.01)
*H05K 3/30* (2006.01)

(52) U.S. Cl.
CPC .............. *G01V 5/0008* (2013.01); *G01T 1/26* (2013.01); *G01V 5/0075* (2013.01); *G01V 13/00* (2013.01); *H05K 3/30* (2013.01); *H05K 3/303* (2013.01); *H05K 2201/10151* (2013.01); *Y02P 70/613* (2015.11)

(58) Field of Classification Search
CPC ................................ G01V 5/0008; G01T 1/26
USPC ........................................................ 250/374
See application file for complete search history.

(56) References Cited

U.S. PATENT DOCUMENTS

| 3,777,221 | A | * | 12/1973 | Tatusko | ............... H01L 23/5384 174/261 |
| 4,685,210 | A | * | 8/1987 | King | ....................... H01Q 1/38 29/830 |
| 5,543,663 | A | * | 8/1996 | Takubo | ............... H01L 23/3675 257/704 |

(Continued)

FOREIGN PATENT DOCUMENTS

GB         2262338 A  *  6/1993

OTHER PUBLICATIONS

M. Alexeev et al., "Development of THGEM-based photon detectors for Cherenkov Imaging Counters", JINST—1st International Conference on Micro Pattern Gaseous Detectors, Jun. 2009, IOP Publishing for SISSA.

(Continued)

*Primary Examiner* — David P Porta
*Assistant Examiner* — Abra Fein
(74) *Attorney, Agent, or Firm* — Intrinsic Law Corp.

(57) ABSTRACT

A detector assembly includes an insulating substrate, a printed circuit board, a resistive, plate, a drilled board, a drift volume, and a cathode. A surface of the printed circuit board exposed to the resistive plate includes printed circuit lines for measuring first and second coordinates of a charge event. A mechanical assembly applies a force between the insulating substrate and the resistive a plate to form an electrical contact between the printed circuit lines on the printed circuit board and the resistive plate without the use of an electrical adhesive.

18 Claims, 13 Drawing Sheets

(56) References Cited

U.S. PATENT DOCUMENTS

| | | | | |
|---|---|---|---|---|
| 7,130,434 | B1* | 10/2006 | Grattan | H04R 1/12 381/113 |
| 7,633,062 | B2 | 12/2009 | Morris et al. | |
| 7,945,105 | B1 | 5/2011 | Jaenisch | |
| 8,288,721 | B2 | 10/2012 | Morris et al. | |
| 8,847,386 | B2* | 9/2014 | Van Veen | H01H 1/021 250/370.01 |
| 8,946,633 | B2* | 2/2015 | Tomioka | G01J 3/0243 250/332 |
| 2001/0040937 | A1* | 11/2001 | Francke | G01T 1/185 378/98 |
| 2003/0020702 | A1* | 1/2003 | Matsuyama | G09G 3/367 345/204 |
| 2009/0183760 | A1* | 7/2009 | Meyer | H01L 31/02008 136/244 |
| 2009/0322649 | A1* | 12/2009 | Hamer | G09G 3/20 345/1.3 |
| 2010/0025800 | A1* | 2/2010 | Kim | H01L 27/14603 257/459 |
| 2011/0133095 | A1* | 6/2011 | Imai | G01T 1/2018 250/370.08 |
| 2015/0108349 | A1 | 4/2015 | Bendahan et al. | |
| 2015/0323492 | A1* | 11/2015 | Mizutani | G01N 27/4071 204/424 |

OTHER PUBLICATIONS

A. Ochi et al., "Micro Pixel Chamber with resistive electrodes for spark reduction", Oct. 22, 2013.
G. Wang et al., "Bayesian Image Reconstruction for Improving Detection Performance of Muon Tomography", IEEE Transactions on Image Processing, May 2009, p. 1080-89, vol. 18, No. 5, IEEE.
C. L. Morris et al., "Horizontal cosmic ray muon radiography for imaging nuclear threats", Nuclear Instruments and Methods in Physics Research, 2014, p. 42-46, B330, Elsevier.
K. N. Borozdin, "Radiographic imaging with cosmic-ray muons", Nature, Mar. 20, 2003, p. 277, vol. 422, Nature Publishing Group.
A. Clarkson et al., "GEANT4 Simulation of a Scintillating-Fibre Tracker for the Cosmic-ray Muon Tomography of Legacy Nuclear Waste Containers", Sep. 2013, p. 1-11.
J. Armitage et al., "First Images from the Cript Muon Tomography System", Applications of Nuclear Techniques, International Journal of Modern Physics: Conference Series, Feb. 2014, vol. 27, World Scientific.
W. B. Gilboy et al., "Industrial radiography with cosmic-ray muons: A progress report", Nuclear Instruments and Methods in Physics Research, May 2007, p. 785-787, No. 580, Elsevier B.V.
H. M. Jaenisch et al, "Real Time Muon Tomography Imaging Simulation and Fast Threat Target Identification", Proc. of SPIE, 2009, vol. 7310, SPIE.
C. L. Morris et al., "Tomographic Imaging with Cosmic Ray Muons", Science and Global Security, 2008, p. 37-53, No. 16, Taylor & Francis Group LLC.
K. Gnanvo et al., "Detection and Imaging of High-Z Materials with a Muon Tomography Station Using GEM Detectors", 2010.
C. L. Morris et al., "Obtaining material identification with cosmic ray radiography", AIP Advances, 2012, AIP Publishing.
M. S. Mitra et al., "Empirical expressions for angular deviation of muons transmitted through slabs of iron, lead and uranium", Nuclear Instruments and Methods in Physics Research A, 2009, p. 684-693, No. 604, Elsevier B.V.
M. Benettoni et al., "Noise reduction in muon tomography for detecting high density objects", Dec. 2013.
R. Oliveira et al., "First Tests of Thick GEMs with Electrodes Made of a Resistive Kapton", Jan. 11, 2007.
S. Pesente et al., "First results on material identification and imaging with a large-volume muon tomography prototype", Nuclear Instruments and Methods in Physics Research A, 2009, p. 738-746, No. 604, Elsevier B.V.
G. Wang et al., "Statistical Image Reconstruction for Muon Tomography Using a Gaussian Scale Mixture Model", IEEE Transactions on Nuclear Science, Aug. 2009, p. 2480-86, vol. 56, No. 4, IEEE.
M. Byszewski et al., "Resistive-strips micromegas detectors with two-dimensional readout", 2nd International Conference on Micro Pattern Gaseous Detectors, Aug. 29-Sep. 1, 2011, IOP Publishing for SISSA.
G. Bencivenni et al., "The Resistive-WELL detector: a compact spark-protected single amplification-stage MPGD", 2014.
A. Di Mauro et al., "Development of innovative micropattern gaseous detectors with resistive electrodes and first results of their applications", 2007.
A. G. Agocs et al., "Study of GEM-like detectors with resistive electrodes for RICH applications", 2007.
R. C. Hoch, "Advances in Cosmic Ray Muon Tomography Reconstruction Algorithms", 2009, Florida Institute of Technology.
D. G. Underwood et al., "RPC Investigation Using Finely Spaced 2-D Strip Readout", IEEE Nuclear Science Symposium Conference Record, 2007, p. 618-622, IEEE.
L. J. Schultz, "Cosmic Ray Muon Radiography", 2003, Portland State University.
S. J. Stanley et al., "See inside: The development of a cosmic ray muon imaging system to aid the clean up of the UK's nuclear waste legacy", Annals of Nuclear Energy, 2008, p. 507-17, No. 35, Elsevier.
L. J. Schultz et al., "Statistical Reconstruction for Cosmic Ray Muon Tomography", IEEE Transactions on Image Processing, Aug. 2007, p. 1985-1993, vol. 16, No. 8, IEEE.
C. Cantini et al., "Long-term operation of a double phase LAr LEM Time Projection Chamber with a simplified anode and extraction-grid design", 2013.
L. Yuanyuan et al., "Imaging Algorithms for Cosmic Ray Muon Radiography Detection of Nuclear Materials", Tsinghua Science and Technology, Jun. 2009, p. 313-321, vol. 14, No. 3.
F. Sauli, "Gas Electron Multiplier (GEM) Detectors: Principles of Operation and Applications", Comprehensive Biomedical Physics, Dec. 2014, vol. 6.
S. Riggi et al., "Muon tomography imaging algorithms for nuclear threat detection inside large volume containers with the Muon Portal detector", Nuclear Instruments and Methods in Physics Research, Jul. 2, 2013.
K. Gnanvo et al., "Imaging of high-Z material for nuclear contraband detection with a minimal prototype of a Muon Tomography station based on GEM detectors", Nuclear Instruments and Methods in Physics Research Section A: Accelerators, Spectrometers, Detectors and Associated Equipment, Oct. 2011.
K. Gnanvo et al., "Large Size GEM for Super Bigbite Spectrometer (SBS) Polarimeter for Hall A 12 GeV program at JLab", Nuclear Instruments and Methods in Physics Research Section A: Accelerators, Spectrometers, Detectors and Associated Equipment, May 11, 2015.

* cited by examiner

LARGE SCALE GAS ELECTRON MULTIPLIER AND DETECTION METHOD

RELATED APPLICATIONS

This application claims the benefit of and priority to U.S. Provisional Application No. 62/091,021, entitled "Large Scale Gas Electron Multiplier and Detection Method," filed on Dec. 12, 2014. This application also claims the benefit of and priority to U.S. Provisional Application No. 62/091,090, entitled "Method and Apparatus for High Atomic Number Substance Detection," filed on Dec. 12, 2014. Each application is incorporated herein by reference.

TECHNICAL FIELD

This application is directed to detectors and methods of detection. More particularly, to detectors, methods of making the same, and methods of using the same in the context of detecting particle interactions with a gas in said detectors. Yet more particularly, the disclosure relates to large scale ionized gas based detectors which can be used in industrial, security, and other applications.

BACKGROUND

Particle detection is a useful tool in many fields of art. In some instances, one or more particles are detected because of an effect they cause when passing through a medium, such as a gas medium. In some applications, a gas is ionized by interactions with a passing or detected particle. The ionization of a detector gas can be amplified with electromagnetic fields and a detector current or signal can be sensed corresponding to the detection of the passing interacting particle. While the present embodiments and examples can be used for detecting muon particles, those skilled in the art will appreciate that the present designs and principles can also be applied to particle (e.g., neutrons, X-Rays, etc.) detection beyond just muon detection. For example, by adding a "neutron conversion" layer of $^6$Li or $^{10}$B just before the detector detailed here.

A THGEM (Thick Gas Electron Multiplier) detector is a robust, simple to manufacture, high-gain gaseous-electron-multiplier detector. Its operation is based on gas multiplication within small, sub-millimeter to one millimeter, diameter holes, in a double-face Cu-clad printed circuit board (PCB). The Cu on each side of the PCB serves as an electrode. The holes are usually made into the PCB, and we refer to this component as a drilled board (DB). An electric potential is applied between the electrodes and creates a strong dipole electric field within the holes, projecting into the adjacent volumes. This shape of the field is responsible for an efficient focusing of ionization electrons into the holes and their multiplication by a gas avalanche process.

In operation, charged particles pass through the gas and ionize it as Minimum Ionizing Particles (MIP). The electrons that result from ionizations in the gas gap above the THGEM drift towards the THGEM holes. The strong dipole electric field established in the holes by the potential difference between the two THGEM faces pulls the electrons into the holes, where they are multiplied in the strong electric field (e.g., 1-5 MV/m). An extraction field in the gap below the THGEM is responsible for the charge collection onto a readout anode/pad.

THGEMs can operate at various gas mixtures such as Ar-, Ne-, or He-based gas mixtures. Examples of mixtures are ArCO2 (90%, 10%) or NeCF4 (95%, 5%). However the final selection of the gas mixture depends on the characteristics of the particles, and the application requirements. In case of cosmic rays muons detection, the actual detector gain and its dynamic range are important. The energy deposited by cosmic ray muons in the gas, which is amplified in the DB, is distributed in a Landau distribution. This means that most of the pulses have a low amplitude and require a high gain to achieve high detection efficiency. However there are sporadic large pulses due the high-energy tail of the distribution that can trigger discharge at high gain of the detector. High dynamic range can be achieved by using Ne or He based mixtures, as they offer higher dynamic range than Ar based mixtures. Ar based mixtures can be used when low gas volumes are needed, as they generates x3 more electrons primaries than Ne based mixtures. However, it is more difficult to avoid discharges (in a THGEM configuration) with using Ar based mixtures.

Imaging requires that the 2D location of the multiplied charge is read out. This is done by reading each coordinate separately, which requires about three times more charge than readout using a pad, and hence better amplification. When the charge is collected directly by the readouts in THGEM, the typical solution is to place thick conductive strips on a PCB, and on them, place thinner strips, each comprising of a conductor and below it an insulator, so that both layers of conductors face the gas. Standard industrial PCB manufacturing techniques may not be able to produce such complex structures. Another solution uses the Resistive Well configuration described below and a two-sided readout PCB, with one side reading the x-coordinates and the other reading the y-coordinate. In this solution, neither layer of readout conductors faces the gas, nor the signals are purely inductive.

When the gas volume below the circuit board and above the readout is omitted, together with the cathode that faced this gas volume, the resulting configuration is known as a well, or a "THWELL." Though the well configuration gives up on the (small) amplification that happens just below the holes in a THGEM, it has the potential to provide stronger signals as the entire avalanche reaches the readout board below. It also simplifies the mechanical structure of the detector and results in a thinner detector. However, since the discharge is cleared through the readouts (and thus, the readout electronics), detectors built in this configuration are likely to be damaged by sparks and, thus, are unreliable.

A variation of THGEM known as Resistive Well includes a resistive layer and an insulating layer below the resistive layer, so the readout is purely inductive. The relevant resistivity for Resistive Well is surface resistivity as the charges collected from the gas are removed to the sides. The Resistive Well configuration can reduce sparking, though the induced charges are somewhat smaller and less focused than the avalanche charges produced in the gas.

Another variation of THGEM known as Resistive Plate Well introduces a resistive plate between the holes and the readout. The relevant resistivity is volume resistivity as the charges collected from the gas are removed through the readout. The Resistive Pate Well configuration can reduce sparking. To ensure good electrical contact between the plate and the readout, the plates are coated with conductive paint and glued to the readouts using conductive epoxy. Using conductive glue is incompatible with detailed readout structures, as needed for 2D readout.

Limitations of a THGEM detector include limited gain and stability due to discharges; centimeter scale boards (e.g., 5 cm) which complicate the mechanical design when trying to develop a large meter scale detector; and large numbers of holes (e.g., pitches between holes of less than 1 mm; hole sizes of about 0.4 mm) which makes the THGEM less cost efficient for larger scale detectors. Manufacturing flaws can occur at the holes due to sharp edges in the copper and the PCB caused by the drilling of the holes, despite attempts to blunt this by etching and other methods to create rims. Hence the yield decreases with the increase in the number of holes, and the price of a working THGEM increases greater than the increase in the number of holes per THGEM. Even if sparking is eliminated, in a Resistive Well or Resistive Plate Well configuration, manufacturing flaws, such as sharp edges, may ionize gas atoms leading to gas avalanches and streamer discharges, which can degrade detection of the signal from the detected particles.

For a large scale muon detector of several square meters, these dimensions and characteristics are not optimized. The small actual size of each THGEM electrode complicates the mechanical design of a large scale detector, influenced the gas distribution and thus distorted the consistency of the measurements. The small holes and the tiny rim affects the stability and gain by generating discharges which limit the electric potential applied between the THGEM electrodes. The relatively thin THGEM board increases the probability of discharges as well as affecting the robustness of the layer—especially for large scale detectors. The relatively small pitch between the holes makes the THGEM less cost efficient for larger scale detectors.

The pitch between holes is a key element in the cost of the THGEM which heavily relies on the number of holes. For example, large a THGEM electrode of one square meter with 1 mm pitch between the holes has a million holes, which makes the THGEM less cost efficient for larger-scale detectors.

It would be desirable to have a detector that overcomes the foregoing limitations.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

In an aspect, the invention is directed to a detector assembly. The assembly includes an insulating substrate having a planar surface. The assembly also includes a printed circuit board (PCB) mounted on the planar surface of the insulating substrate, the PCB having opposing first and second surfaces, the first surface exposed to the insulating substrate, the second surface including printed circuit lines. The assembly also includes a resistive plate disposed on and in direct physical contact with the second face of the PCB. The assembly also includes a drilled board disposed on the resistive plate. The assembly also includes a cathode disposed above the drilled board, the cathode defining a drift volume between the cathode and the drilled board, the drilled board disposed between the drift volume and the resistive plate. The assembly also includes a mechanical assembly connected to the insulating substrate and the resistive plate, wherein the mechanical assembly applies a force between the insulating substrate and the resistive plate to form an electrical contact between the printed circuit lines on the PCB and the resistive plate.

In another aspect, the invention is direct to a detector module. The detector module includes a hollow body configured to retain a gas. The detector module also includes a plurality of modular detector assemblies disposed in the body. Each module detector assembly includes an insulating substrate having a planar surface. Each module detector assembly also includes a printed circuit board (PCB) mounted on the planar surface of the insulating substrate, the PCB having opposing first and second surfaces, the first surface exposed to the insulating substrate, the second face including printed circuit lines. Each module detector assembly also includes a resistive plate disposed on and in direct physical contact with the second face of the PCB. Each module detector assembly also includes a drilled board disposed on the resistive plate. Each module detector assembly also includes a cathode disposed above the drilled board, the cathode defining a drift volume between the cathode and the drilled board, the drilled board disposed between the drift volume and the resistive plate. Each module detector assembly also includes a mechanical assembly connected to the plastic stage and the insulating substrate, wherein the mechanical assembly applies a force between the insulating substrate and the resistive plate to form an electrical contact between the printed circuit lines on the PCB and the resistive plate.

In another aspect, the invention is directed to a method of manufacturing a detector assembly. The method includes mounting a printed circuit board (PCB) on a planar surface of an insulating substrate, the PCB having opposing first and second surfaces, the first surface exposed to the insulating substrate, the second face including printed circuit lines. The method also includes placing a resistive plate in direct physical contact with the second face of the PCB. The method also includes disposing a drilled board on the resistive plate. The method also includes disposing a cathode above the drilled board, the cathode defining a drift volume between the cathode and the drilled board, the drilled board disposed between the drift volume and the resistive plate. The method also includes applying a force between the insulating substrate and the resistive plate to form an electrical contact between the printed circuit lines on the PCB and the resistive plate.

IN THE DRAWINGS

For a fuller understanding of the nature and advantages of the present invention, reference is being made to the following detailed description of preferred embodiments and in connection with the accompanying drawings, in which.

DETAILED DESCRIPTION

The present disclosure overcomes some or all of the limitations of the THGEM and its various configurations as discussed above. In an aspect, the disclosure provides a charged particle detector that can operate on a large scale (e.g., 5-25 square meters) for detecting cosmic rays. In particular, this disclosure provides systems and methods for detecting cosmic muons as they enter and exit some volume to be scanned, such as a shipping container or a truck, for dangerous high-Z materials (e.g., radioactive and nuclear materials). The detector can operate at a relatively low flux rate (e.g., about 130 Hz/square meter muons) and can have an adequate spatial resolution (e.g., about 2-5 mm) to detect such high-Z materials. Reference will be made to an exemplary detector called a Well with Imaging and Resistive Plate (WIRP), though the disclosure is not limited to such a detector. The charged particle detector can detect muons, neutrons, and other charged particles.

Figure 1:
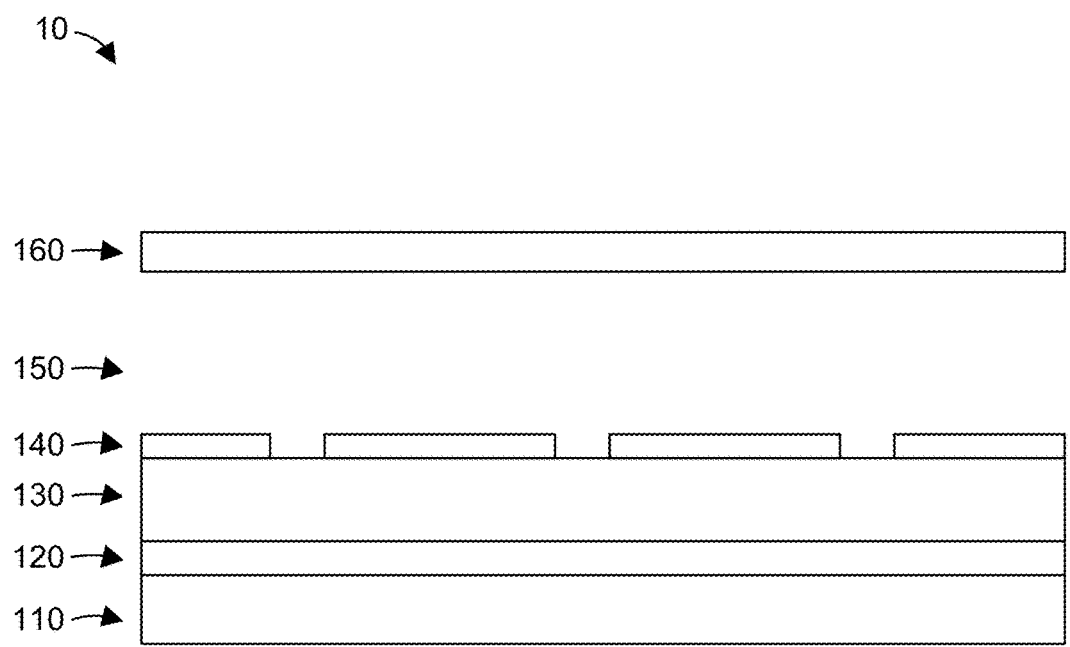
FIG. 1 is a side view of a detector assembly according to an embodiment.

FIG. 1 illustrates a side view of a detector assembly 10 according to an embodiment. The detector 10 includes a plastic stage 110, a printed circuit board (PCB) 120, a resistive plate 130, a drilled board 140, a drift volume 150, and a cathode 160.

The circuit board 120 is disposed on the plastic stage 110. The plastic stage 110 receives an external force (e.g., from screws, bolts, a clamp, a mechanical assembly) to press the circuit board 120 towards the resistive plate 130 (or vice versa). In some embodiments, the plate 130 includes holes for receiving screws or bolts that are driven between the plastic stage 110 and the plate 130. The holes can be disposed along a perimeter of the stage 110 and/or on its interior surface. This mechanical force can create electrical contact between the circuit lines on the circuit board 120 and the resistive plate 130. This is an advantage over the prior art approach of adhering a circuit board to a resistive plate with conductive glue/epoxy. The mechanical force can also fix the position and orientation of the circuit board 120 relative to the plastic stage 110 and the resistive plate 130. Thus, the mechanical force can maintain alignment of the readout lines on the circuit board 120 with the resistive plate 130 and the drilled board 140. In addition, the plastic stage 110 can distribute the external mechanical force across the circuit board 120 to prevent bending or cracking of the circuit board 120 or damage to its electrical contacts. In some embodiments, alternative materials can be used to contrast the plastic stage 110. For example, the plastic stage 110 can be formed out of any rigid and insulating material, such as the epoxy substrates used for a printed circuit boards, a ceramic (e.g., alumina, berrylia, etc.) substrate, or similar materials.

Figure 1A:
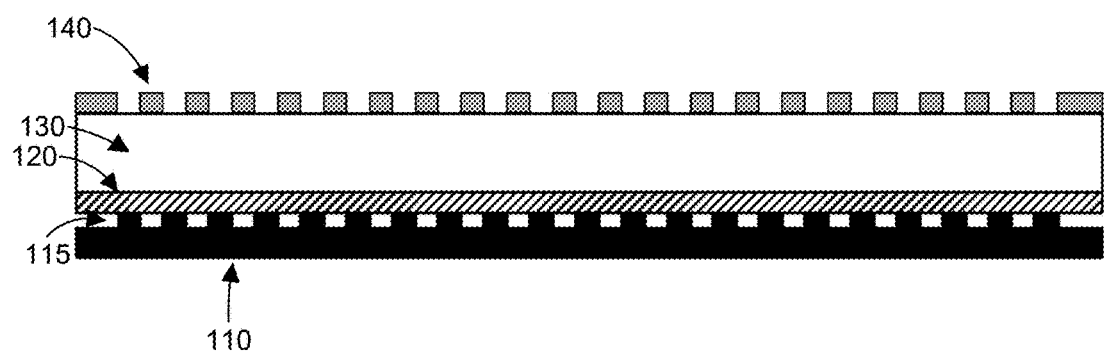
FIG. 1A is a side view of a portion of a detector according to an embodiment.

As illustrated in FIG. 1A, in some embodiments, the plastic stage 110 can have flat bumps 115, which are aligned to concentrate the pressure on the circuit board 120 directly below the holes in the drilled board 140. For example, the bumps can have the same diameter as the holes in the drilled board 140, resulting in a pressure that is over four times larger than the pressure of the equivalent construction without any bumps 115.

Returning to FIG. 1, the printed circuit board 120 is disposed between the plastic stage 110 and the resistive plate 130. The readout lines in the circuit board 120 face the resistive plate 130 and thus directly collect the charges produced in the gas for both the x and y coordinates. The PCB 120 can be manufactured using industry standard techniques.

The circuit board 120 includes circuit lines running along a surface of the circuit board 120 that faces the resistive plate 130. The circuit lines include first circuit lines for measuring a first coordinate (e.g., the "x" coordinate) and second circuit lines for measuring a second coordinate (e.g., the "y" coordinate). The first and second circuit lines can have various orientations with respect to each other. For example, the first and second circuit lines can be disposed orthogonally to each other (e.g., along the vertical and horizontal axes), at a 45-degree angle with respect to each other, a 30-degree angle with respect to each other, a 10-degree angle with respect to each other, or any other orientation. For example, some circuit lines can run parallel to the x axis of the circuit board 120 (horizontally in FIG. 1) to measure the y coordinate and some circuit lines can run parallel to the y axis (vertically in FIG. 1) to measure the x coordinate. The circuit lines that measure the x and y coordinates can be configured in a comb-like pattern. The circuit lines can be aligned with the holes in the drilled board 140.

Figure 2:
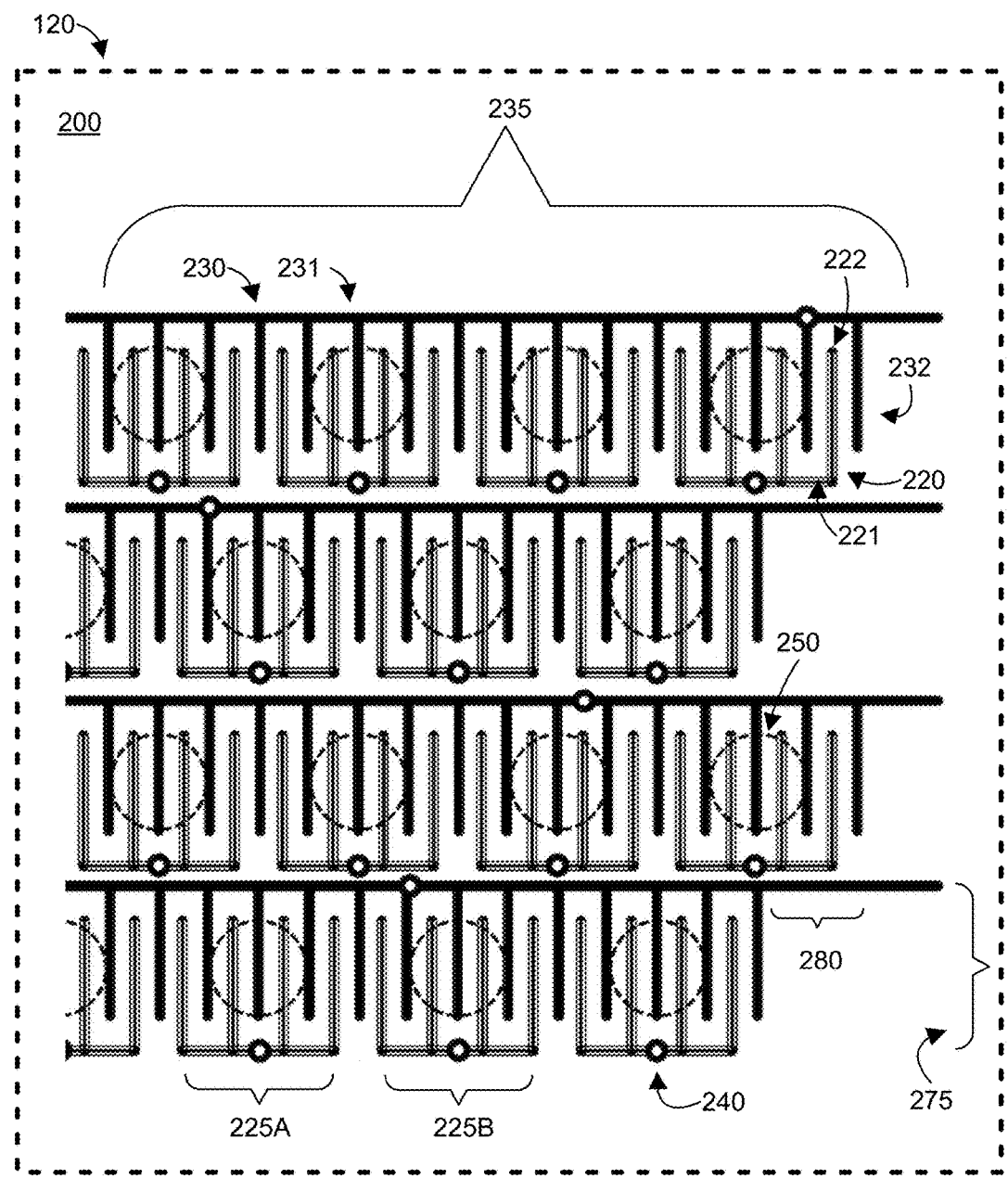
FIG. 2 is a top view of a circuit board from FIG. 1 according to an embodiment.

FIG. 2 illustrates a top view of circuit board 120. The "top" 200 of the circuit board 120 faces the resistive plate 130 while the "bottom" of the circuit board 120 faces the plastic stage 110. An array of circuit lines 220 that measure the x coordinates and an array of circuit lines 230 that measure the y coordinates are disposed on the top 200 of circuit board 120. The circuit lines 220, 230 are generally arranged in a comb-like pattern having intermingling or alternating teeth. The circuit lines 220 that measure the x coordinates include horizontal line portions 221 and teeth 222. The horizontal line portions 221 and teeth 222 are orthogonal to one another. The circuit lines 230 that measure the y coordinates include horizontal lines 231 and teeth 232. The horizontal lines 231 and teeth portions 232 are orthogonal to one another. In some embodiments, the horizontal line portions 221 and teeth 222 are oriented at an angle between 0 and 90 degrees with respect to on another, for example 30 degrees, 45 degrees, 60 degrees, or any angle therebetween. In some embodiments, the horizontal line portions 231 and teeth 232 are oriented at an angle between 0 and 90 degrees with respect to on another, for example 30 degrees, 45 degrees, 60 degrees, or any angle therebetween. Likewise, the combs 225, 235 can be oriented at an angle between 0 and 90 degrees with respect to on another, for example 30 degrees, 45 degrees, 60 degrees, or any angle therebetween As illustrated, the horizontal line portions 221 of circuit lines 220 are discontinuous across a row 275 and thus form discrete combs 225A, 225B, 225n (in general, "x" combs 225). In contrast, the horizontal lines 231 are continuous along a row 275 with teeth 232 disposed along the length of horizontal lines 231 to form a continuous "y" comb 235. Although the horizontal line portions 221 are illustrated as discontinuous and the horizontal lines 231 are illustrated as continuous in FIG. 2, it is noted that the structure can also be reversed. In other words, the circuit lines 220 that measure the x coordinates can have continuous horizontal lines while the circuit lines 230 that measure the y coordinates can have discontinuous line portions. Each comb 225, 235 is connected to a respective readout line on the bottom of the circuit board 120 through respective vias 240.

The combs 225, 235 are aligned with the holes 250 in the drilled board 140, which are projected onto the top 200 of the circuit board in FIG. 2 for illustration purposes. Due to the alignment, two teeth 222 of the "x" comb 225 and one tooth 232 of the "y" comb 235 are disposed below each hole 250 in drilled board 140. In some embodiments, a different number of teeth 222 are disposed below each hole 250. For example, in some embodiments, two "x" teeth 222 and two "y" teeth 232 are disposed below each hole 250. Alternatively, in some embodiments, one "x" tooth 222 and two "y" teeth 232 are disposed below each hole 250. As each tooth 222, 232 can detect an electron avalanche (caused by a muon ionizing gas in the drift volume 150) that occurs near it, and as the width of the avalanches is limited, and as detection in both coordinates is required to locate the avalanche, the efficiency of the detector 10 will be low when the density of the teeth 222, 232 is too low. However, the density of teeth 222, 232 can be limited by manufacturing and/or cost constraints.

In some embodiments, the alignment of the circuit lines 220, 230 with the holes 250 in the drilled board 140 can include horizontal offsets 280 to compensate for the pattern of holes 250, which can be disposed in a hexagonal or nearly-hexagonal grid, such as a honeycomb pattern. In some embodiments, a pin (e.g., a plastic pin) can be inserted through the circuit board 120 to fix its horizontal position so the drilled board 140 can be aligned with the readout lines in the circuit board 120. In some embodiments, the circuit board 120 and the drilled board 140 are mechanically connected, for example, through one or more screws, to further secure their alignment. The mechanical connection also provides electrical contact between the circuit lines 220, 230 in circuit board 120 and the resistive plate 130 beneath each hole 250 without needing a conductive adhesive, as discussed above.

Figure 3:
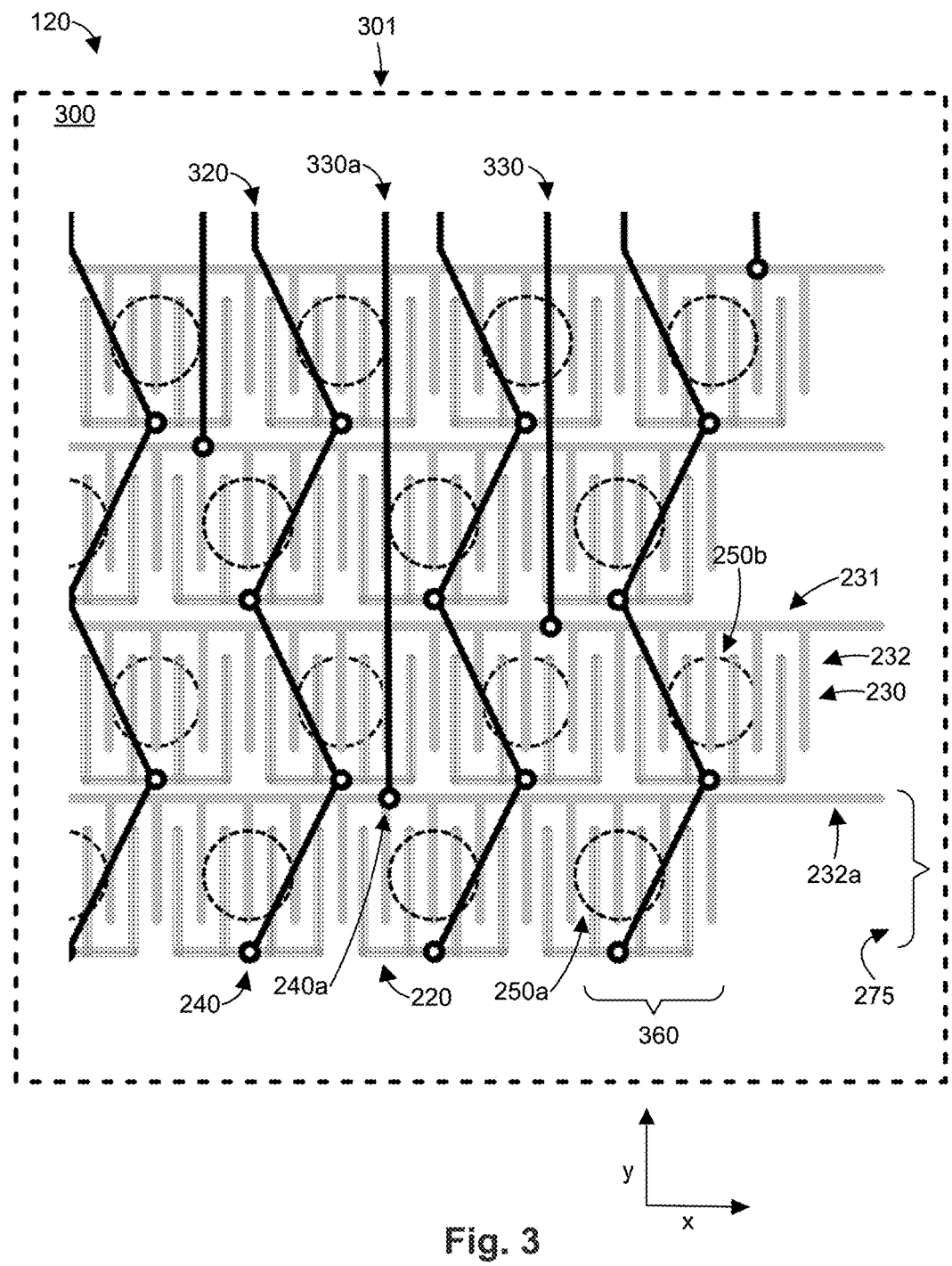
FIG. 3 is a bottom view of a circuit board from FIG. 1 according to an embodiment.

FIG. 3 illustrates a bottom view of circuit board 120. The "bottom" 300 of the circuit board 120 faces the plastic stage 110. A plurality of "x" readout-lines 320 and "y" readout lines 330 are disposed on the bottom 300 of circuit board 120. Although not normally visible from the bottom 300 of the circuit board 120, circuit lines 220, 230 and holes 250 in drilled board 140 are illustrated in FIG. 2 as projections of the respective structures for illustration purposes. The readout lines 320, 330 are connected to respective circuit lines 220, 230 by vias 240, as discussed above. The "x" readout lines 320 form a zig-zag pattern as they extend between vias 240 along a column 360 of holes 250a, 250b. The holes 250a, 250b are offset horizontally (in the "x" direction") because the holes 250 are arranged in a honeycomb pattern. However, the holes 250 can be arranged in other patterns as discussed below. The "y" readout lines 330 extend from a via 240 connected to line 231 which extends across a given row 275 on the top 200 of the circuit board 120. The readout lines 320, 330 can be can be narrow (e.g. about 0.25 mm) to reduce capacitance. As used herein, "about" means plus or minus 10% of the relevant number or value (e.g., about 10 means between 9-11).

Thus, the readout lines 320, 330 can output a signal that represents the position (i.e., row 275 and column 360) of the electron avalanche created at drilled board 140 due to an ionization in the drift gap 150 by a particle (e.g., a muon). The charge is amplified in a hole 250 and is detected by respective circuit lines 220, 230 on the top 200 of the circuit board 120. Two or more detectors 10 can be used to measure the position of the particle at two locations to reconstruct a segment of the particle's path.

In some embodiments, one or more metal pins extend from the resistive plate 130 to one or both readout lines 320, 330. The pins can contact the resistive plate 130 beneath each hole 250 in the drilled board 140. For example, a first pin can contact the "x" readout line 320 beneath a first hole 250 and a second pin can contact the "y" readout line 330 beneath the first hole 250. Such contact between the readout lines 320, 330 and the resistive plate 130 can improve electrical contact between the resistive plate 130 and the circuit board 120.

The horizontal lines 231 can be read out on the side edge of the top 200 of the circuit board 120. In that embodiment, the readout lines 330 are not needed. As illustrated in FIGS. 2 and 3, however, the horizontal lines 231 are connected through vias 240 to readout lines 330 that extend in a vertical direction (i.e., in the "y" direction orthogonal to the horizontal lines 231) on the bottom of the board 120 and, therefore, the readout lines 330 can be readout at the upper or lower edge of the board 120. The horizontal line portions 221 on the top 200 of the circuit board 120 are connected through vias 240 to readout lines 320 that extend vertically in a zig-zag arrangement on the bottom 300 of the board 120 and, therefore, the readout lines 320 can be readout at the upper or lower edge of the board 120. In some embodiments, the circuit board 120 can only be readout at a single edge, for example, if the readout lines 320 or 330 extend to the upper edge but not the lower edge of board 120.

Figure 4:
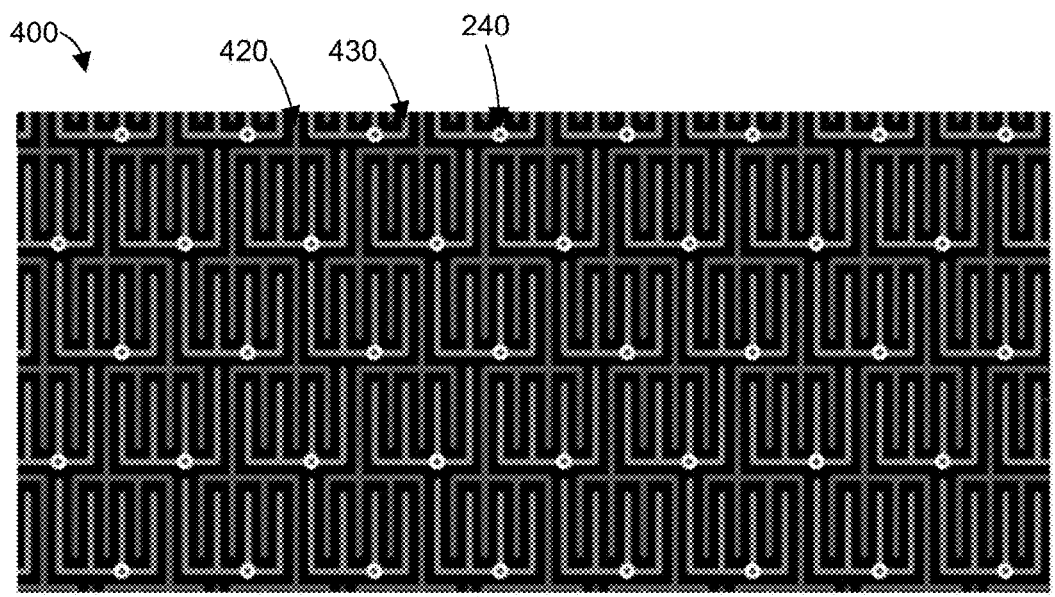
FIG. 4 illustrates an alternative embodiment of a circuit board from FIG. 1.

In another embodiment, illustrated in FIG. 4, all the readout lines can be connected along the left and/or the right edge of the circuit board 120. This is accomplished by introducing additional vias 140 that connect the readout lines running along the front side 400 to orthogonal readout lines running on the backside 300 to the desired edge of the board. In FIG. 4, the dark lines 420 measure the x coordinate and the light lines 430 measure the y coordinate. It is noted that the dark lines 420 and the light lines 430 both include discontinuous horizontal lines in contrast to FIGS. 2 and 3 in which the "x" horizontal lines 221 are discontinuous while the "y" horizontal lines 231 are continuous.

Connecting the readout lines to a single edge of the circuit board 120 allows multiple circuit boards 120 to be modularly arranged next to one another in a large detector configuration. This is an advantage over prior art systems where the "x" coordinates readouts connected on a first edge and the "y" coordinates readouts connected on a second edge of a circuit board, which meant that only 4 of such circuit boards could be arranged next to one another (to provide the two exposed edges for the readouts).

The locations of the vias 240 can be optimized according to the size of the detector. For large detectors, it is desirable to minimize the longest readout path. One way to reduce the readout path is by connecting the horizontal lines 232 that are furthest from the edge of the board 140 where the readout connections are made with vias placed near the center of the respective horizontal lines 232. For example, the horizontal line 232a is connected to via 240a at approximately the midpoint or center of the horizontal line. Thus, the longest readout path would be from the edge of horizontal line 232a (i.e., about half the width of the board 140 along the top 200) through via 240a to readout line 330a, which extends to edge 301 (i.e., about the full length of the board 140 along the bottom 300).

In some embodiments, the size and density of the combs 225, 235 can be limited due to crosstalk and/or interference, that can occur between adjacent horizontal lines 231 or adjacent readout lines 320, 330 if the distance between them is small (e.g., less than 1 mm). To reduce such crosstalk/interference, the spacing between adjacent readout lines 320, 330 can be increased. For example, the readout lines 330 can be arranged in a zigzag pattern to follow the readout lines 320. Alternatively, the vias 240 can be positioned so that the both readout lines 320, 330 form straight lines (or substantially straight lines).

Returning to FIG. 1, the resistive plate 130 is disposed between the printed circuit board 120 and the drilled board 140. The resistive plate 130 can be made from a plastic polymer designed for electrostatic discharge. In some embodiments, the resistive plate 130 is between about 0.4 mm and 4 mm in thickness, for example about 0.4 mm, about 0.6 mm, or about 4 mm in thickness. In other embodiments, the thickness of plate 130 is greater than 4 mm, which can correspond to the thickness of readily available plates of such materials, such as SEMITRON® ESD 225 (available from Quadrant Plastics Composites Inc.).

The presence of the resistive plate 130 allows the detector to operate with large electric fields (e.g. 5 MV/m) without suffering from sparks. In particular, even cosmic muons that ionize many electrons, leading to larger electron showers, are unlikely to result in a spark. With these large electric fields, the detector can provide robust amplification with large gains (e.g., $10^4$-$10^6$). Large detectors generally require large gains since their readout strips have higher capacitance and thus require larger signal charges.

The drilled board 140 is a printed circuit board with a plurality of holes defined therein. The drilled board 140 can be a single-faced copper-clad printed circuit board having an epoxy substrate (e.g., FR-4). The copper thickness can be chosen according to industry standards, such as 17 microns or 35 microns. In some embodiments, the drilled board 140 is formed of multiple sub-units of identical drilled boards to provide a scalable configuration. For example, the drilled board 140 can be formed of a 4×4 array of modular drilled boards.

Figure 5:
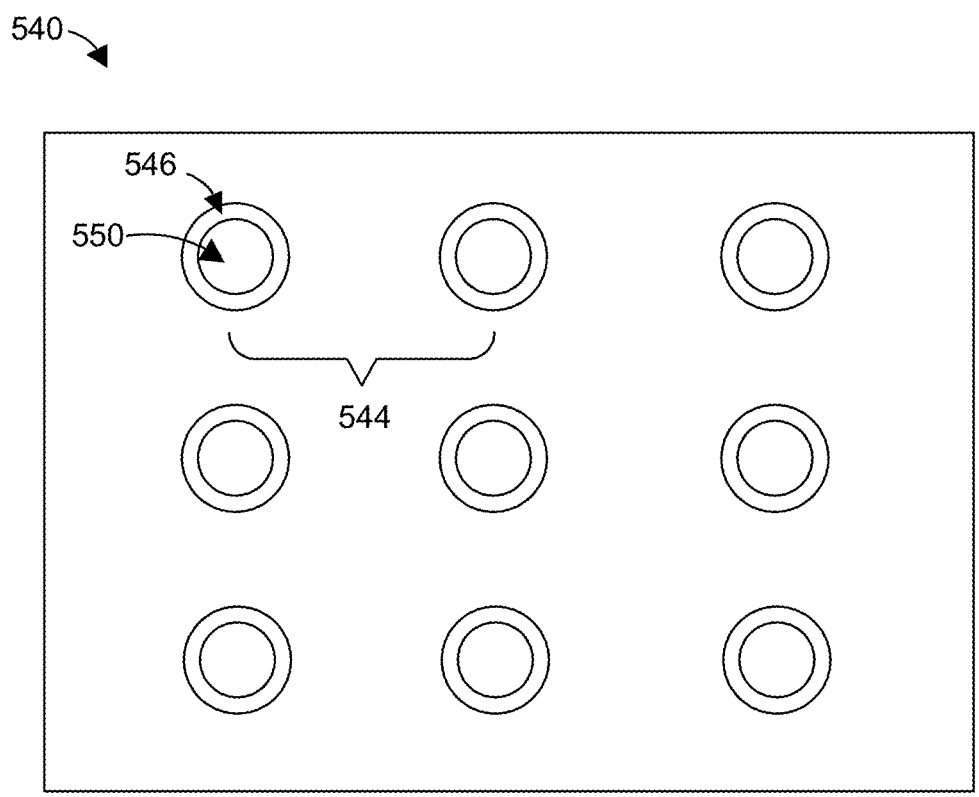
FIG. 5 is a top view of a drilled board according to an embodiment.

FIG. 5 is a top view of a drilled board 540 according to an embodiment. The drilled board 540 includes a plurality of holes 550, as discussed above. The holes 550 can be formed by mechanically drilling the board 540 or through punching. After the holes 550 are formed, they can be chemically etched to dull any sharp edges to reduce streamer discharges.

The holes 550 can have a pitch 544 (i.e., distance between centers of adjacent holes 550) of about 2 mm to about 5 mm, which is 3-5 times higher than the pitch used in prior art systems. This increase in pitch results in a corresponding decrease (by 10-25 times) in the number of holes, which reduces manufacturing cost. The increase in pitch can also improve the detector stability. Since discharge occurs within the holes, reducing the number of holes reduces the probability of discharges and allows operation at higher voltages, thus improving the multiplication gain. In some embodiments, the pitch 544 is about 3 mm or about 4 mm.

If higher spatial resolutions are desired, pitches as small as 0.8 mm can be produced. As notes above, costs can rise rapidly with the number of holes, so small pitches are most useful when the desired detector area is small.

The holes 550 are arranged in a pattern or a grid, as illustrated in FIGS. 2, 3, and 5. In some embodiments, the holes 550 are arranged in a hexagonal, or almost hexagonal pattern, as illustrated in FIGS. 2 and 3. A hexagonal pattern can provide better coverage of the drilled board 540, which can provide enhanced electron collection efficiency. The holes 550 can have a diameter between about 0.4 mm and about 3 mm. Standard drill diameters, such as 1 mm, 1.5 mm, etc. are preferred.

Figure 6:
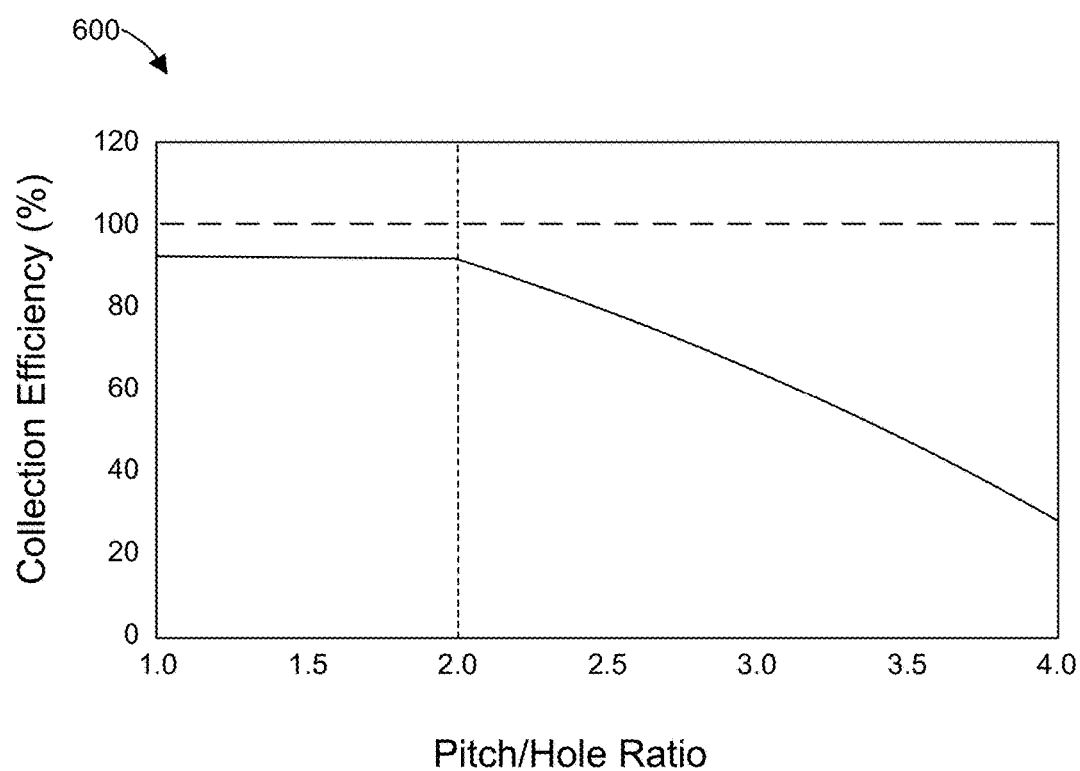
FIG. 6 is a graph formed as a result of a simulation collecting randomly-generated particles using a drilled particle board with holes having various diameters and pitches.

The ratio of the pitch 244 to the diameter of the holes 550 can vary from around 1.4 to 3 including 2. Higher ratios create larger electric fields in the holes and thus stronger amplification; however, they can also lower the electron collection efficiency. FIG. 6 is a graph 600 formed as a result of a simulation collecting randomly-generated particles using the drilled particle board 540 with holes 550 having various diameters and pitches 544. As indicated in the graph 600, the electron collection efficiency is at its maximum value (about 90%) when the pitch/hole ratio is less than or equal to 2.0. In the preferred embodiment, the pitch is twice the hole diameter. For example, the standard drill diameter of 1.5 can be matched to a pitch of 3 mm.

Figure 7:
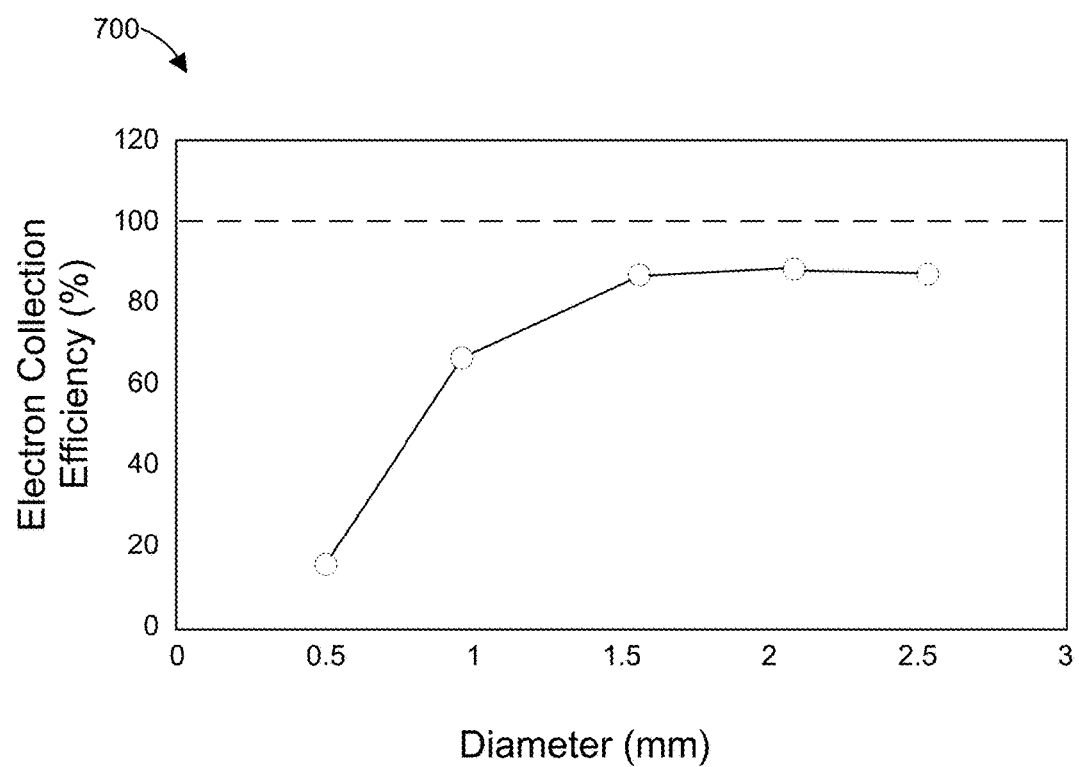
FIG. 7 is a graph of hole diameter in a drilled particle board against electron collection efficiency.

FIG. 7 is a graph 700 based on the same simulation described above. The graph 700 plots the diameter of the holes 550 against the electron collection efficiency. For each diameter, the pitch 544 remained constant at 3.0 mm. As illustrated in the graph 700, the collection efficiency reaches a maximum when the diameter is greater than or equal to 1.5 mm, which corresponds to a pitch/hole ratio of less than or equal to 2.0, as discussed above.

Returning to FIG. 5, a clearance ring 546 is formed at the edge of the hole 550. The ring 546 is a narrow region (e.g., about 100 microns to about 200 microns) surrounding the perimeter of the hole 550 where the metal (e.g., copper) has been removed, for example by chemical etching. The removal of metal can eliminate any sharp edges on the perimeter of the hole 550, which can appear as a result of drilling the holes 550. When an etching process is used, the initial thickness of the copper can be about 140 microns, aiming for about 35 microns after etching. Alternatively, the clearance ring 546 can be formed before the hole 550 is drilled, to avoid creating sharp copper edges during the drilling.

Returning to FIG. 1, the cathode 160 is disposed above the drilled board 140, the space between the cathode 160 and the drilled board 140 defining the drift volume 150. The detector 10 is placed in a sealed volume filled with gas, filling the drift volume 150 and the holes in the drilled board 140. The gas can include Ar, Ne, and/or He. For example, the gas can be 90% Ar and 10% $CO_2$, 30% Ar and 70% $CO_2$, or 95% Ne and 5% $CF_4$. The gas can have a pressure slightly above atmospheric pressure, e.g., 1.005-1.03 bar at sea level. The cathode 160 applies a voltage across the drift volume 150 to the drilled board 140. The voltage is chosen to yield a drift field of 0.1-1 kV/cm.

In operation, a charged particle (e.g., muon) passing through the drift volume 150 ionizes the gas therein. The drift field in the drift volume 150 pushes the electrons towards the drilled board 140. The large field in the holes of the drilled board 140 guides the electrons into the holes where they create electron avalanches. The resulting charge flows through the resistive plate 130 and is conducted by the readout PCB 120 toward the readout electronics, which typically reside outside the gas volume.

Figure 8:
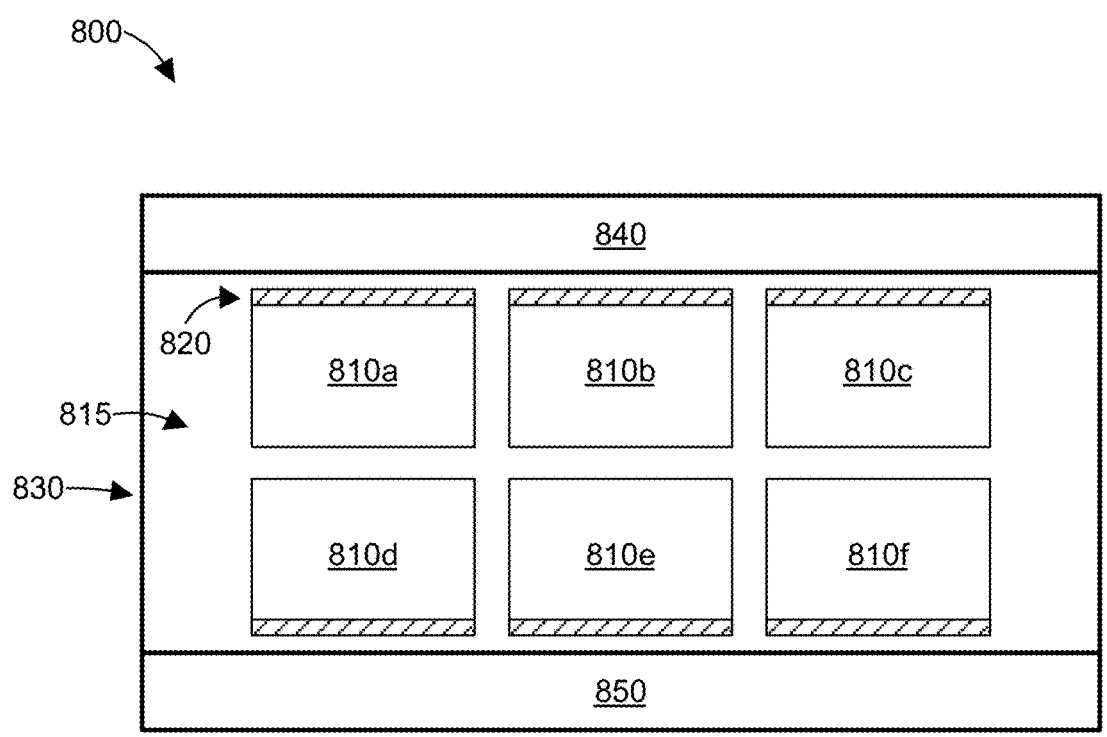
FIG. 8 is a block diagram of a detector module for detecting charged particles according to an embodiment.

FIG. 8 is a block diagram of a detector module 800 for detecting charged particles. The module 800 includes an 3×2 array of detector units 810*a*, 810*b*, 810*c*, 810*d*, 810*e*, and 810*f* (generally detector units 810). The module 800 is scalable as fewer or additional detector units 810 can be included. The detector units 810 are the same or substantially the same as the detector unit 10 described above. Each detector unit 810 is configured to have an analog readout 820 on a single edge of the respective detector unit 810. The readout 820 can be an exposed edge of the circuit board (e.g., circuit board 120) where the readout lines terminate. The analog readouts 820 are connected to electronics boxes 840, 850. The electronics boxes 840, 850 each include a control panel, communications interfaces, front end units (FEUs) which digitize the signals collected through the readouts 820, and one or more processors or field programmable gate arrays (FPGAs). The control panel can include controls for the DC voltage applied to the detector units and for gas flow to the module 800. The communications interfaces can include Ethernet ports, WiFi transceivers, or other communications interfaces to communicate with the detectors 810. The communications interfaces can also include a PC interface to connect to a computer, a server, etc.

The detector units 810 are disposed in a housing that defines a gas volume 815 to retain a gas. The gas can be an Ar-, Ne-, or He-based gas mixtures, for example ArCO2 (90%, 10%) or NeCF4 (95%, 5%). The housing 830 can be formed out of a metal or it can be lined with a metal. If the housing 830 is lined with metal, the body of the housing can be an insulator. The metal can shield the readout lines 220, 230, 320, 330 on the circuit board from external electric noise, thus less than 1 mm of an excellent conductor such as iron can be used, while poorer conductors such as aluminum require a thickness above 1 mm. If a thin metallic layer (e.g., 1 mm) is used with an insulating housing, the metal can be either internal to the insulating housing, which protects it from the outside environment, or it can be external to the insulating housing, which reduces the possible paths for unwanted discharges within the gas volume.

Figure 9:
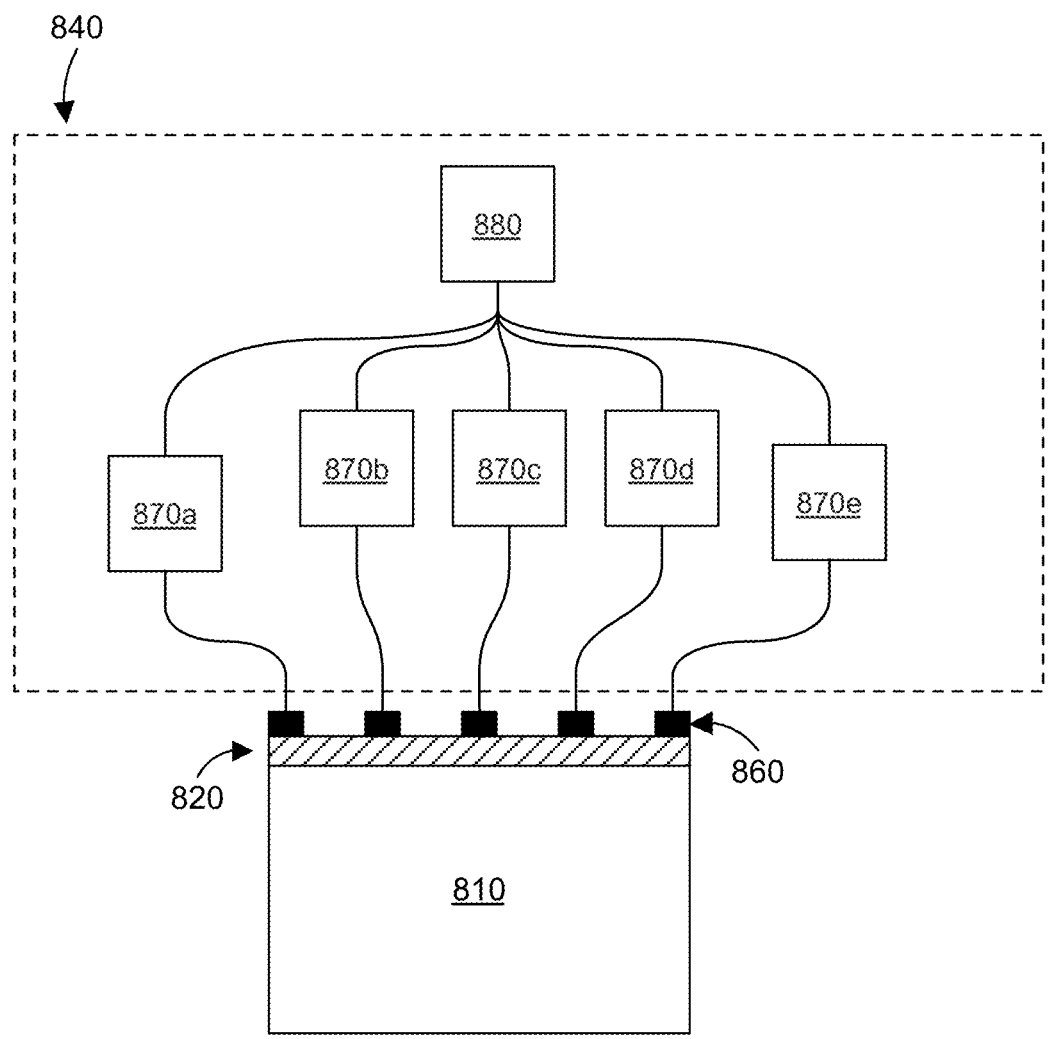
FIG. 9 is a block diagram of a representative portion of the detector module illustrated in FIG. 8.

FIG. 9 is a block diagram of a representative portion of the module 800 illustrated in FIG. 8. The block diagram illustrates a series of connectors 860 in electrical communication with the electronic readout 820. Each connector 860 is assigned a channel (e.g., a range of signals) from the electrical readout 820. Each connector 860 is in electrical communication with a respective FEU 870*a-e* (in general, FEU 870). The FEUs 870 are each in electrical communication with a processor or FPGA 880 (herein FPGA 880). Although FIG. 9 illustrates only a single detector 810, it is noted that the structure of FIG. 9 can apply to all detectors 810 described above with respect to FIG. 8. The FEUs 870 can be placed near, but outside, the gas volume 815, as illustrated in FIG. 9, or they can be placed within the gas volume 815. For example, the FEUs 870 can be located beside the readout PCB (e.g., circuit board 120) and connect to its edge. Alternatively, the FEUs 870 can be integrated into the readout PCB (e.g., circuit board 120) and be similarly located on its periphery.

For each channel, the relevant FEU 870 (*a*) passes the signal through a protection circuit, which can blocks any DC current or abnormally large current spike originating from the detector 810, (b) amplifies the signal, (c) shapes the signal, (d) digitizes the signal in an analog to digital converter, and (e) in parallel to (d), compares the analog signal to a trigger voltage threshold and appropriately raises a trigger for that channel. The voltage threshold can be set to filter most (e.g., at least 95%, 98%, 99%, or 99.9%) of the transient noise from the detector 810. In some embodiments, the voltage threshold is set to about 1-2 V.

The FPGA 880 controls data flowing to and from the FEUs 870. For example, the FPGA 880 can send a signal to the FEUs 870 to set one or more parameters of each FEU 870. The parameters can include the trigger voltage threshold for the FEUs 870 as described above, the duration of the signal integration window, which channels may participate in the trigger, etc. When the FPGA 880 receives an output trigger signal from a given FEU 870, the FPGA 880 checks for a local coincidence with respect to the output trigger signal. To do so, the FGPA 880 checks whether the FEU 870 received a signal above the trigger voltage threshold in both the x and y coordinate readouts from the same detector 810 within a predetermined time period (e.g., between about 25 ns and 200 ns). If the local coincidence check fails (e.g., a signal was received in the x coordinate readout but not the y coordinate readout), the FPGA 880 determines that the output trigger signal occurred due to electronic noise from the detector 810 or module 800. If the local coincidence check passes (i.e., a signal was received in both the x and y coordinate readouts), the FPGA 880 determines that the trigger signal is valid and then sends a signal to all FEUs 870 to report the signals from their respective channels. The FPGA 880 can then send the data reported from the FEUs 870 to a computer or server via a PC interface in the electronics box 840. In addition to the charge/signal data from the FEUs 870, the FPGA 880 can also send monitoring data for the detector such as data from temperature sensors, pressure sensors, voltage sensors, and/or settings of the FEUs 870. In some embodiments, when the FPGA 880 determines that the local coincidence check passes, the FPGA 880 sends a signal to all other FPGAs in a larger system to request that those FPGAs report the data measured by their respective FEUs.

In some embodiments, the FEUs 870 are disposed on the face of the PCB (e.g., PCB 120) of each detector 810 that is exposed to the plastic stage 110. This allows the respective readout lines to be shorter since they connect with the FEUs 870 on the PCB and do not need to extend along the connectors 860 to the electronics box 840.

In some embodiments, the FEUs 870 are placed within the gas volume 815 and are integrated into the readout PCB 120, with their components placed on the backside (i.e. facing away from the resistive plate 130 and drilled board 140) of the PCB 120. Connectors 860 to the FEUs 870 are placed on the PCB 120 so each readout line ("x" or "y") is connected through a connector 860 to an FEU 870. However, the PCB 120 should not be pushed against the resistive plate 130 in the area dedicated to the components of the FEUs 870. For example, the plastic stage 110 can have depressions in its face aligned with the components of the FEUs 870, or the entire FEUs 870, that prevent or minimize contact between the stage 110 and the sensitive parts of the FEUs 870 on the readout PCB 120.

Figure 9A:
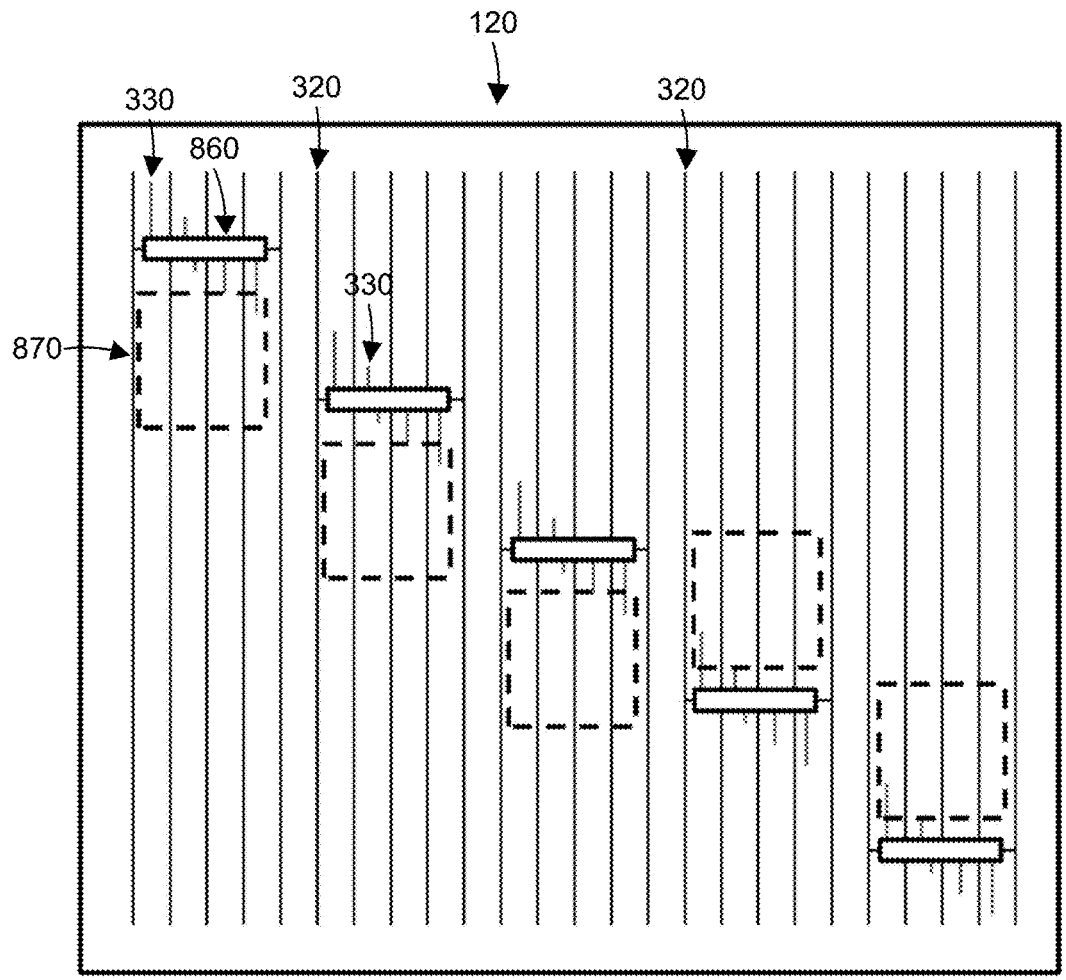
FIG. 9A illustrates a backside of a printed circuit board according to an embodiment.
Figure 9B:
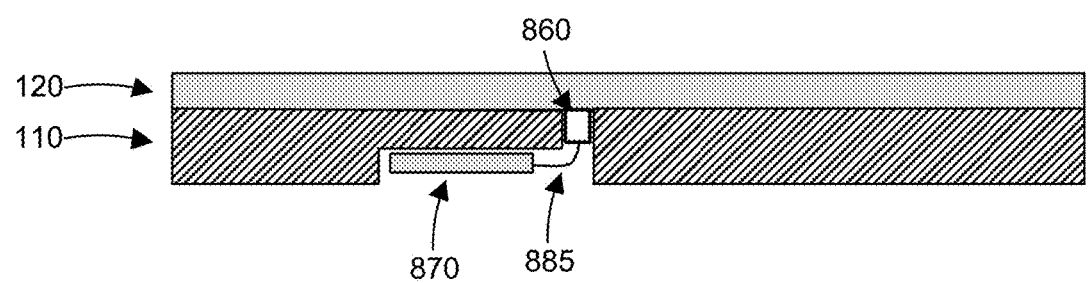
FIG. 9B is a side view of a portion detector assembly according to an embodiment.

Alternatively, the FEUs 870 can be connected directly or through flexible ribbons to the readout lines. Connecting the FEUs 870 to the readout lines 890 directly or through flexible ribbons allows the respective readout lines to be shorter since they do not need to extend along the connectors 860 to the electronics box 840. FIG. 9A illustrates a direct connection of the FEUs 870 to the "x" and "y" readout lines 320, 330, respectively, on PCB 120 using connectors 860. Furthermore, placing the FEUs 870 within the readout PCB 120 allows particularly short readout lines for the coordinate whose lines run on the front of the readout PCB 120 (In FIG. 9A, these are the readout lines 330 for the "y" coordinate readout). As illustrated in FIG. 9B, the connection through flexible ribbons 885 allows for a compact arrangement of the FEUs 870 within the plastic stage 110.

Figure 10:
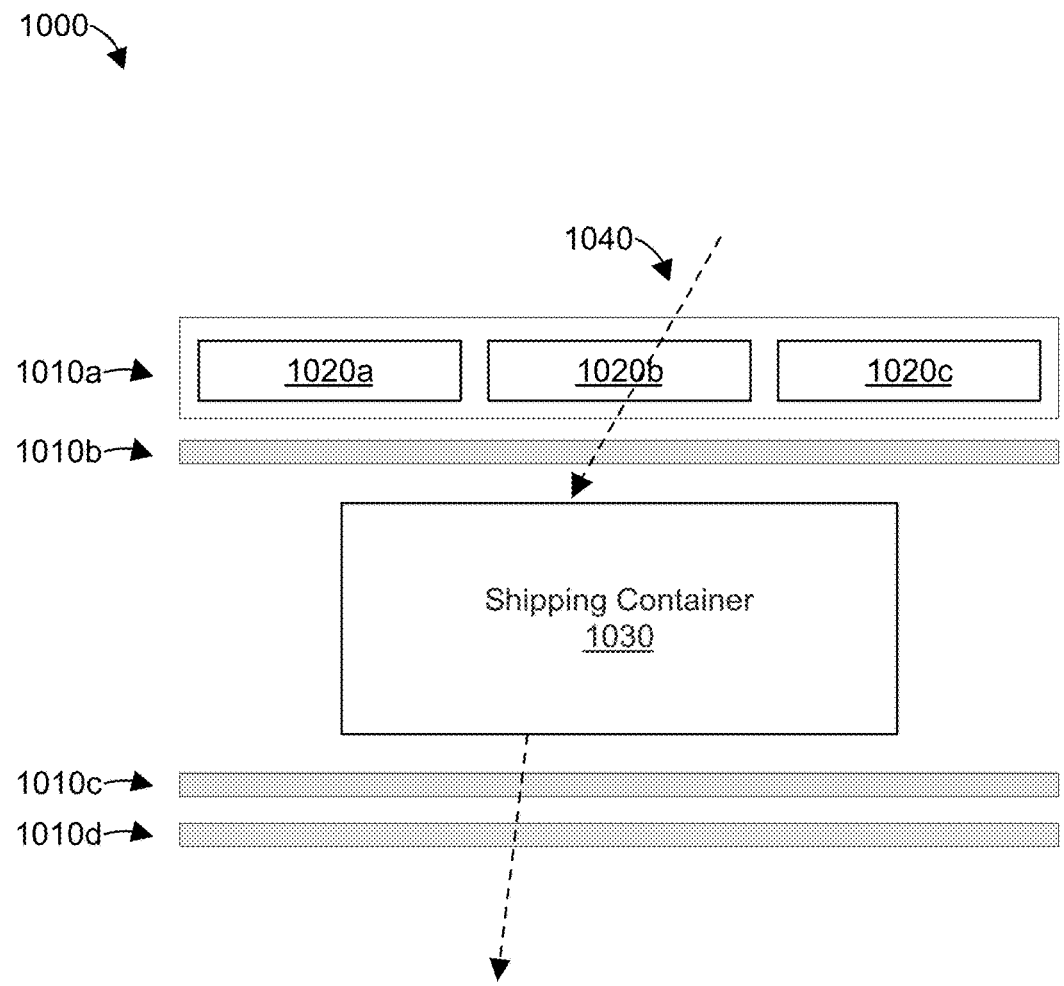
FIG. 10 is a block diagram of a detection system according to an embodiment.

FIG. 10 is a block diagram of a detection system 1000. The detection system 1000 includes a first detection layer 1010a, a second detection layer 1010b, a third detection layer 1010c, and a fourth detection layer 1010d (in general, detection layer 1010). Additional detector layers (not shown in FIG. 10) can be included to improve the tracking above and below the container, and/or as part of a spectrometer that measures the muon's energy. The first detection layer 1010a includes a first detector module 1020a, a second detector module 1020b, and a third detector module 1020c (in general, detector module 1020). Each detector module 1020 includes an array of detectors, for example as described above with respect to FIGS. 8 and 9. Although only illustrated with respect to the first detector layer 1010a, each detector layer 1010 includes a plurality of detector modules 1020. The detector modules 1020 allow the detector layers 1010 to be big enough to scan a large volume such as a shipping container or a truck 1030.

In operation, a muon 1040 (or other charged particle) passes through first and second detector layer 1010a, 1010b. The muon 1040 proceeds to the shipping container 1030 where the muon 1040 is typically deflected based on the cargo in the shipping container. The deflected muon 1040 exits the shipping container 1030 and passes through third and fourth detector layers 1010c, 1010d. Each detector layer 1010 can be measure the x and y coordinates of the muon 1040 in the x-y plane of the respective detector layer 1010. Thus, the x and y coordinates of the first and second detector layers 1010a, 1010b can be used to measure the incoming trajectory of the muon 1040. Similarly, the x and y coordinates of the third and fourth detector layers 1010c, 1010d can be used to measure the outgoing trajectory of muon 1040 after it is deflected by cargo in the shipping container 1030.

In some embodiments, a local coincidence check can be used across detector modules 1020 in a given detector layer 1010. For example, a local FPGA for detector module 1020a can determine whether there was a valid local coincidence in detector module 1020a. If so, the local FPGA can send a signal to the FPGAs for detector modules 1020b, 1020c, which in turn can send signals to retrieve data from their respective FEUs. In addition or in the alternative, the local FPGA for detector module 1020a can send a signal to all FPGAs for detector modules 1020 in each detector layer 1010, which in turn can send signals to retrieve data from their respective FEUs.

In some embodiments, a global coincidence check can be made using detectors in multiple detector layers 1010. For example, a central FPGA can determine whether there was a valid local coincidence in first and second detector layers 1010a, 1010b. If so, the central FPGA can send a global trigger to all FPGAs in each detector layer 1010, which in turn can send signals to retrieve data from their respective FEUs.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. A detector assembly comprising:
    an insulating substrate having a planar surface;
    a printed circuit board (PCB) mounted on the planar surface of the insulating substrate, the PCB having opposing first and second surfaces, the first surface exposed to the insulating substrate, the second surface including printed circuit lines;
    a resistive plate disposed on and in direct physical contact with the second face of the PCB;
    a drilled board disposed on the resistive plate;
    a cathode disposed above the drilled board, the cathode defining a drift volume between the cathode and the drilled board, the drilled board disposed between the drift volume and the resistive plate;
    a mechanical assembly connected to the insulating substrate and the resistive plate, wherein the mechanical assembly applies a force between the insulating substrate and the resistive plate to form an electrical contact between the printed circuit lines on the PCB and the resistive plate;
    wherein the drilled board includes a plurality of holes, the holes extending through the drilled board to expose portions of the resistive plate; and
    wherein a pitch between adjacent holes is about 2 mm to about 5 mm.

2. The detector assembly of claim 1, wherein the mechanical assembly includes at least one of screws or bolts.

3. The detector assembly of claim 1, wherein the insulating substrate has raised bumps that contact the printed circuit board, the bumps focusing a pressure on corresponding regions of the printed circuit board.

4. The detector assembly of claim 1, wherein the plurality of holes are arranged in a hexagonal pattern.

5. The detector assembly of claim 1, wherein a ratio of a pitch between adjacent holes and a diameter of each hole is about 2.

6. The detector assembly of claim 1, wherein the printed circuit lines include first and second circuit lines, the first circuit lines for detecting a charge in a first direction, the second circuit lines for detecting a charge in a second direction, wherein the first direction is different than the second direction.

7. The detector assembly of claim 6, wherein, the first direction is orthogonal to the second direction.

8. The detector assembly of claim 6, wherein the first and second circuit lines on the second surface of the PCB are in electrical communication with respective readout lines on the first surface of the PCB.

9. The detector assembly of claim 6, wherein the first circuit lines are configured in a first shape of first combs having first teeth and the second circuit lines are configured in a second shape of second combs having second teeth, the first teeth interleaved with the second teeth.

10. The detector assembly of claim 1, wherein the insulating substrate comprises plastic.

11. A detector assembly comprising:
    an insulating substrate having a planar surface;
    a printed circuit board (PCB) mounted on the planar surface of the insulating substrate, the PCB having opposing first and second surfaces, the first surface exposed to the insulating substrate, the second surface including printed circuit lines;
    a resistive plate disposed on and in direct physical contact with the second face of the PCB;
    a drilled board disposed on the resistive plate;
    a cathode disposed above the drilled board, the cathode defining a drift volume between the cathode and the drilled board, the drilled board disposed between the drift volume and the resistive plate;
    a mechanical assembly connected to the insulating substrate and the resistive plate, wherein the mechanical assembly applies a force between the insulating substrate and the resistive plate to form an electrical contact between the printed circuit lines on the PCB and the resistive plate;

wherein the printed circuit lines include first and second circuit lines, the first circuit lines for detecting a charge in a first direction, the second circuit lines for detecting a charge in a second direction, wherein the first direction is different than the second direction;

wherein the first and second circuit lines on the second surface of the PCB are in electrical communication with respective readout lines on the first surface of the PCB; and wherein the readout lines are arranged to match a pattern of holes defined in the drilled board.

12. The detector assembly of claim 11, further comprising metal vias that extend from the printed circuit lines on the second surface to the respective readout lines on the first surface.

13. The detector assembly of claim 11, wherein the readout lines can be read out only from a single edge of the PCB.

14. The detector assembly of claim 11, wherein the readout lines can be read from connectors placed on the PCB.

15. The detector assembly of claim 11 wherein flexible ribbons connect the PCB to front end electronic units through respective gaps defined in the insulating substrate.

16. The detector assembly of claim 11, wherein the pattern of holes is a hexagonal pattern and the readout lines can be read out only from a single edge of the PCB.

17. A detector module comprising:
a hollow body configured to retain a gas; and
a plurality of modular detector assemblies disposed in the body, each modular detector assembly comprising:
an insulating substrate having a planar surface;
a printed circuit board (PCB) mounted on the planar surface of the insulating substrate, the PCB having opposing first and second surfaces, the first surface exposed to the insulating substrate, the second face including printed circuit lines;
a resistive plate disposed on and in direct physical contact with the second face of the PCB;
a drilled board disposed on the resistive plate;
a cathode disposed above the drilled board, the cathode defining a drift volume between the cathode and the drilled board, the drilled board disposed between the drift volume and the resistive plate;
a mechanical assembly connected to the insulating substrate and the resistive plate, wherein the mechanical assembly applies a force between the insulating substrate and the resistive plate to form an electrical contact between the printed circuit lines on the PCB and the resistive plate;
wherein each modular detector assembly includes a second drilled board, the second drilled board disposed on the resistive plate adjacent to the first drilled board.

18. The detector module of claim 17, wherein a plurality of bumps are disposed on the planar surface of the insulating substrate.

* * * * *